(12) United States Patent
Reddy et al.

(10) Patent No.: US 9,771,325 B2
(45) Date of Patent: Sep. 26, 2017

(54) TRICYCLIC COMPOUNDS AND PREPARATION THEREOF

(71) Applicant: Council of Scientific & Industrial Research, New Delhi (IN)

(72) Inventors: Dumbala Srinivasa Reddy, Pune (IN); Kashinath Komirishetty, Pune (IN); Prakash Daulat Jadhav, Pune (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 15/118,990

(22) PCT Filed: Feb. 13, 2015

(86) PCT No.: PCT/IN2015/000085
§ 371 (c)(1),
(2) Date: Aug. 15, 2016

(87) PCT Pub. No.: WO2015/121876
PCT Pub. Date: Aug. 20, 2015

(65) Prior Publication Data
US 2016/0362371 A1    Dec. 15, 2016

(30) Foreign Application Priority Data
Feb. 14, 2014 (IN) ............... 0421/DEL/2014

(51) Int. Cl.
C07D 209/48    (2006.01)
C07D 209/70    (2006.01)

(52) U.S. Cl.
CPC ......... *C07D 209/48* (2013.01); *C07D 209/70* (2013.01)

(58) Field of Classification Search
None
See application file for complete search history.

(56) References Cited

U.S. PATENT DOCUMENTS

2006/0276497 A1    12/2006    Chatterjee et al.

FOREIGN PATENT DOCUMENTS

WO    0185686 A2    11/2001
WO    2008063644 A1    5/2008

OTHER PUBLICATIONS

Xu Zhen-Yu, et al., "A novel norsesquiterpene alkaloid from the mushroom-forming fungus*Flammulina velutipes*," Chinese Chemical Leters, Elsevier Ltd., vol. 24, No. 1, pp. 57-58 (2013).
Tao M., et al., "Synthesis and structure-activity relationships of novel poly(ADP-ribose) polymerase-1 inhibitors," Bioorganic & Medical Chemistry Letters, vol. 16, No. 4, pp. 938-942 (2006).
Yuanzhen Li, et al., "Efficient Synthesis of maleimides and carbazoles via Zn(DTf) 2-Catalyzed tandem annulations of isonitriles and allenic esters," Organic Letters, vol. 9, No. 20, pp. 4057-4060 (2007).
Sambasivarao Kotha, et al., "Diversity-oriented approach to novel spirocyclics via enyne metathesis, diels-alder reaction, and a [2+2+2] cycloaddition as key steps," vol. 24, No. 15, pp. 1921-1926 (2013).
Le Guillanton, et al., "N Deg 120.—Utilisation de la cyclopentylidene-2 cyclopentanone a la preparation de derives decahydro as-indaceniques et hexahydro as-indaceniques. III.—Preparation de derives hexahydro-1, 2, 3, 6, 7, 8 as-indaceniques," Bulletin De La Societe Chimique De France, pp. 630-638 (1963).
Wells G.J., et al., "Synthesis and structure-activity relationships of novel pyrrolocarbazole lactam analogs as potent and cell-permeable inhibitors of poly(ADP-ribose) polymerase-1 (PARP-1)," Bioorganic & Medical Chemistry Letters, vol. 16, No. 5, pp. 1151-1155 (2006).
Dunn, et al. "Novel poly(ADP-ribose) polymerase-1 inhibitors," Bioorganic & Medical Chemistry Letters, vol. 17, No. 2, pp. 542-545 (2007).
Dunn, et al., "Serendipitous discovery of a prodrug of a PARP-1 inhibitor," Chemical Biology & Drug Design, vol. 82, No. 3, pp. 348-350 (2013).
K. Kashinath, et al., "Total synthesis of an anticancer norsequiterpene alkaloid isolated from the fungus *Flammulina velutipes*," Organic & Biomolecular Chemistry, vol. 12, No. 24, pp. 4098 (2014).
Juergen Ramharter, et al., "From planning to optimization: total synthesis of valerenic acid and some bioactive derivatives," European Journal of Organic Chemistry, vol. 2012, No. 10, pp. 2041-2053 (2012).
Imahori, et al., "Acceleration effect of allylic hydroxy group on ring-closing enyne metathises of terminal alkynes: scope and application to the synthesis of isofagomine," Tetrahedron Letters, vol. 49, No. 2, pp. 265-268 (2007).
ISA/EP International Search Report and Written Opinion prepared for PCT/IN2015/000085 dated Jun. 3, 2015.

*Primary Examiner* — Brian J Davis
(74) *Attorney, Agent, or Firm* — McDonald Hopkins LLC

(57) ABSTRACT

The present invention provides novel tricyclic compound of Formula I or its stereoisomer or ester or pharmaceutically acceptable salts and preparation thereof useful for treatment of cancer.

11 Claims, No Drawings

TRICYCLIC COMPOUNDS AND PREPARATION THEREOF

FIELD OF THE INVENTION

The present invention relates to novel tricyclic compounds of formula I or its stereoisomer or ester or pharmaceutically acceptable salts and preparation thereof useful in treatment of cancer.

BACKGROUND AND PRIOR ART OF THE INVENTION

Chemotherapy is still an important option for the treatment of various types of cancers. The chemotherapeutic drugs preferentially target tumor cells and act by impairing mytosis by various mechanisms including damaging DNA and inhibition of the cellular machinery involved in cell division.

Continuous research work for new cytotoxic agents with unique mechanisms of action is carried worldwide to develop novel potent and selective anti-cancer agents.

One of the oldest and most effective strategies for developing new chemotherapeutic drugs is the isolation and evaluation of chemicals present in natural form. The importance of natural products for drug discovery has been impressive and there are a large number of active drugs used in cancer therapy which are based on natural products.

Pyarrocarbazoles, Phenothiazidines, nitrogen containing heterocyclic compounds of natural origin are known to possess cytotoxic activity. Norsesquiterpenes and sesquiterpenesare a class of naturally occurring molecules that have demonstrated therapeutic potential in decreasing the progression of cancer. These alkaloids are isolated from both plant and marine life and are modulated in the art for treatment of cancer.

Kai-Shun Bi et al. in an article titled "A novel norsesquiterpene alkaloid from the mushroom-forming fungus Flammulinavelutipes" in Chinese Chemical Letters 2013, 24, 57-58 reports the isolation of novel tricyclic compound (1) from the solid culture of mushroom-forming fungus Flammulinavelutipes fermented on rice. According to this article the compound showed cytotoxicity against KB cells in vitro with an $IC_{50}$ value of 16.6 μmol/L.

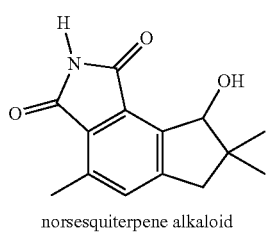

norsesquiterpene alkaloid
Anti cancer activity
$IC_{50}$ = 16.6 μmol/L (KB cells)

1

-continued

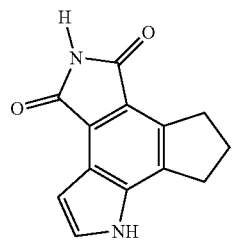

PARP-1 (poly(ADP-ribose) polymerase-1) inhibitor
$IC_{50}$ = 40 nmol/L

2

In addition to this in literature related compounds are also known for PARP-1 (poly(ADP-ribose) polymerase-1) inhibition. M. Tao et al. in an article titled "Synthesis and structure-activity relationships of novel poly(ADP-ribose) polymerase-1 inhibitors" reported compound 2 as PARP-I inhibitor in Bioorg. Med. Chem. Lett. 2006, 16, 938-942. Also several related compounds of structure 2 are claimed in a patent publication, US 2006/0276497 A1.

Article titled 'Serendipitous Discovery of a Prodrug of a PARP-1 Inhibitor' by Derek Dunn, Jean Husten et al published in Chem Biol Drug Des 2013; 82: 348-350 discloses a series of N-alkyl analogs of compound 1 and compound 2 having anticancer activity;

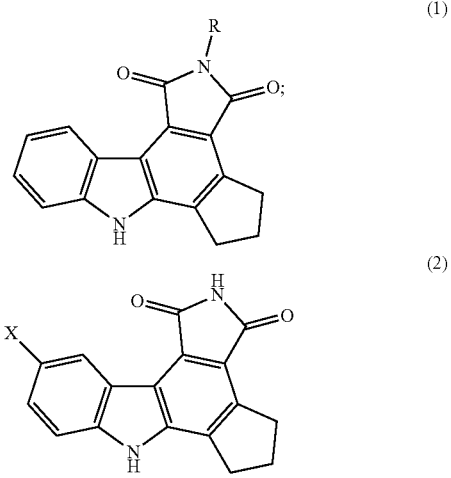

wherein,
X=CH$_2$NH$_2$.

Although, new chemotherapeutic agents are continuously developed, many of them have not been therapeutically useful due to low tumor selectivity and harsh side effects.

Thus there remains a need in the current scenario to provide novel anti-cancer compounds which have potent and selective activity towards tumor cells.

The present invention is thus directed to meet the above requirements by providing novel heterocyclic compounds from sesquiterpene class of alkaloids as potent anti-cancer agents.

OBJECTS OF THE INVENTION

It is the primary objective of the present invention to provide novel tricyclic compounds of formula I or its stereoisomer or ester or pharmaceutically acceptable salts and preparation thereof, for use in the treatment of cancer.

SUMMARY OF THE INVENTION

In an aspect, the present invention provides novel tricyclic compounds of Formula I or its stereoisomer or esters or pharmaceutically acceptable salts thereof,

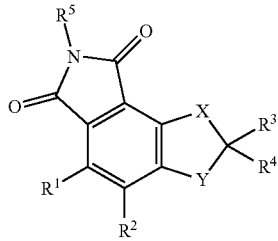

Formula I wherein,

X and Y represent the group C(O) or CRaRb;

Ra and Rb are independently selected from H, alkyl, aralkyl, OR, NR'R" or Ra and Rb together optionally form a 3-7 membered cyclic ring which optionally contain a hetero atom selected from O, N or S;

Ra or Rb optionally form a cyclic ring with $R_3$ or $R_4$;

$R_1$ and $R_2$ are independently selected from H, alkyl, aryl, aralkyl, hydroxyalkyl, alkoxyalkyl, nitro, cyano, OR, NR'R" or R1 and R2 together optionally form a 3-7 membered cyclic ring which optionally contain a hetero atom selected from O or S;

$R_3$ and $R_4$ are independently selected from H, alkyl, aryl, aralkyl, hydroxyalkyl, alkoxyalkyl, COORa, C(O)R, C(O)NR'R" or $R_3$ and $R_4$ together optionally form a 3-7 membered cyclic ring which optionally contain a hetero atom selected from O, N or S;

R, R' and R" are selected from the group consisting of H, alkyl, aryl, aralkyl and acyl; and $R_5$ is independently selected from the group consisting of H, alkyl, alkenyl, alkynyl, aryl, aralkyl, alkylsulfonyl, arylsulfonyl, hydroxyalkyl and alkoxyalkylacyl.

In another aspect, the compounds of Formula I are selected from the group consisting of 8-(Benzyloxy)-4,7,7-trimethyl-7,8-dihydrocyclopenta[e]isoindole-1,3(2H,6H)-dione(7);

8-Hydroxy-4,7,7-trimethyl-7,8-dihydrocyclopenta[e]isoindole-1,3(2H,6H)-dione (8);

Diethyl 1,3-dioxo-2,3,6,8-tetrahydrocyclopenta[e]isoindole-7,7(1H)-dicarboxylate (18);

Diethyl2-(2-hydroxyethyl)-1,3-dioxo-2,3,6,8-tetrahydrocyclopenta[e]isoindole-7,7(1H) -dicarboxylate (19);

Diethyl 4-methyl-1,3-dioxo-2,3,6,8-tetrahydrocyclopenta[e]isoindole-7,7(1H)-dicarboxylate (22);

Diethyl 2-(2-hydroxyethyl)-4-methyl-1,3-dioxo-2,3,6,8-tetrahydrocyclopenta[e]isoindole-7,7(1H)-dicarboxylate (23);

Diethyl 2-((4-fluorophenyl)sulfonyl)-4-methyl-1,3-dioxo-2,3,6,8-tetrahydrocyclopenta[e]isoindole-7,7(1H)-dicarboxylate (24);

(5bS,6aR)-5-hydroxy-6,6-dimethyl-5b,6,6a,7-tetrahydro-1H-cyclopropa [3,4]cyclopenta [1,2-e]isoindole-1,3(2H)-dione (28);

5-nitro-7,8-dihydrocyclopenta[e]isoindole-1,3(2H,6H)-dione (30);

4-nitro-7,8-dihydrocyclopenta[e]isoindole-1,3(2H,6H)-dione (31);

5-amino-7,8-dihydrocyclopenta[e]isoindole-1,3(2H,6H)-dione (32); and 5-((3-methoxyphenyl)amino)-7,8-dihydrocyclopenta[e]isoindole-1,3(2H,6H)-dione (33).

In yet another aspect, the present invention provides a process for preparation of tricyclic compounds of formula I or its stereoisomer or ester or pharmaceutically acceptable salts thereof, comprising the steps of;

a. degassing a mixture of compound II

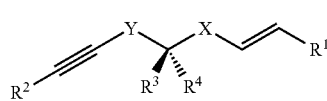

II in toluene in a stream of argon and treating with Grubbs' I generation catalyst with stirring to obtain a mixture;

b. adding freshly distilled DMAD and DDQ to the mixture of step (a) followed by purification to obtain intermediate compound of Formula III

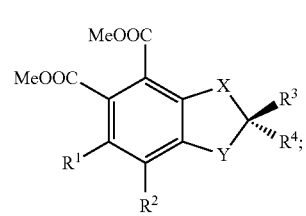

III c. adding KOH to a solution of intermediate compound of Formula III in EtOH-water mixture with stirring followed by heating the mixture with ethylene glycol and urea at a temperature in the range of 150-200° C. to afford compound of Formula I.

The general process is depicted in Scheme I:

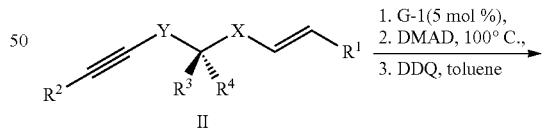

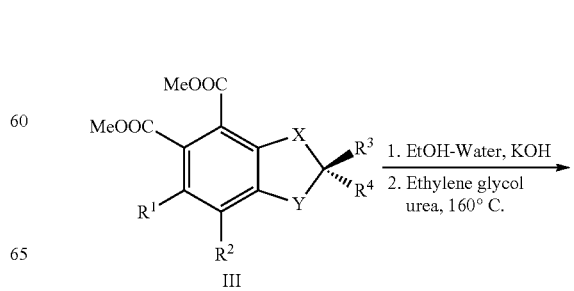

III

-continued

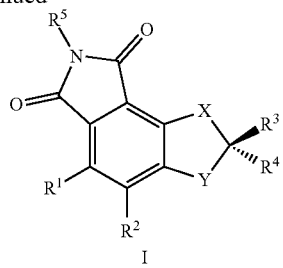

I wherein,

X and Y represent the group C(O) or CRaRb;

Ra and Rb are independently selected from H, alkyl, aralkyl, OR, NR'R" or Ra and Rb together optionally form a 3-7 membered cyclic ring which optionally contain a hetero atom selected from O, N or S;

Ra or Rb optionally form a cyclic ring with R3 or R4;

R1 and R2 are independently selected from H, alkyl, aryl, aralkyl, hydroxyalkyl, alkoxyalkyl, nitro, cyano, OR, NR'R" or R1 and R2 together optionally form a 3-7 membered cyclic ring which optionally contain a hetero atom selected from O or S;

R3 and R4 are independently selected from H, alkyl, aryl, aralkyl, hydroxyalkyl, alkoxyalkyl, COORa, C(O)R, C(O)NR'R" or R3 and R4 together optionally form a 3-7 membered cycle which optionally contain a hetero atom selected from O, N or S;

R, R' and R" are selected from the group consisting of H, alkyl, aryl, aralkyl and acyl;

R5 is independently selected from the group consisting of H, alkyl, alkenyl, alkynyl, aryl, aralkyl, alkylsulfonyl, arylsulfonyl, hydroxyalkyl and alkoxyalkylacyl.

In an aspect, the present invention provides preparation of compounds (7) and (8) by the general process comprising;
  a. degassing a mixture of compound (5) in toluene by passing stream of argon and treating with Grubbs'I generation catalyst with stirring at a temperature in the range of 30-60° C. to obtain a mixture;
  b. adding freshly distilled DMAD and DDQ to mixture of step (a) to afford product (6);
  c. adding KOH to a solution of compound (6) of step (b) in EtOH-water mixture with stirring to obtain crude 3-(benzyloxy)-5-(methoxycarbonyl)-2,2,6-trimethyl-2,3-dihydro-1H-indene-4-carboxylic acid;
  d. taking crude product of step (c) in ethylene glycol and adding urea with heating to afford pure 8-(benzyloxy)-4,7,7-trimethyl-7,8-dihydrocyclopenta[e]isoindole-1,3(2H,6H)-dione (7);
  e. deprotecting benzyl group of compound (7) of step (d) with 10% Pd/C in ethanol to obtain racemate compound (8).

In another aspect, the present invention provides a process for preparation of compounds (18), (19), (22), (23) and (24) from the compound (16) and compound (20) respectively. The compounds (16) and (20) are prepared by a process known in the art (reference of which is provided herein below in the description) and comprises Tandem Enyne, Diene-ene Metathesis Reaction and Diels Alder reaction.

In yet another aspect, the present invention provide a process for synthesis of compound (28) from compound (25), wherein the compound (25) is prepared by a known process (reference of which is provided herein below in the description) Compound 25 was prepared using zonolysis of (+)—3 carene to afford keto aldehyde followed by aldol-type cyclization.

In another aspect, the present invention provides a process for synthesis of compounds (30), (32) and (33) from compound (29) which is a known compound. The compound (29) is prepared by a process (reference of which is provided herein below in the description) which include Diels-Alder reaction with neat maleimide, followed by DDQ oxidation to obtain pyrrolocarbazole (29).

In another embodiment of the invention, a pharmaceutical composition is provided comprising an effective amount of compound of claim 1 optionally along with a pharmaceutically acceptable carrier.

In yet another embodiment of the invention, the compound is for use in the treatment of cancer.

Abbreviations:
DMAD: Dimethyl acetylenedicarboxylate
DDQ: 2,3-Dichloro-5,6-dicyano-1,4-benzoquinone.
XPHOS: 2-Dicyclohexylphosphino-2',4',6'-triisopropylbiphenyl

DETAILED DESCRIPTION OF THE INVENTION

The present invention will now be described in detail with reference to preferred or optional embodiments so that the various aspects therein will be more clearly understood and appreciated.

The present invention relates to novel tricyclic compounds of Formula I or its stereoisomers or esters or pharmaceutically acceptable salts, comprising;

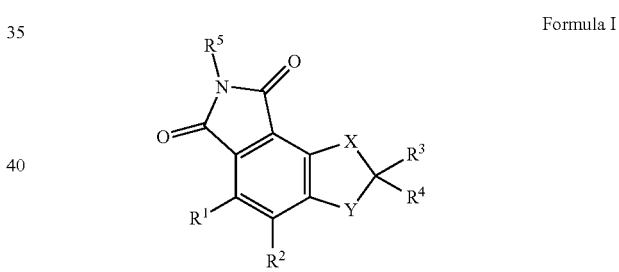

Formula I wherein:

X and Y represent the group C(O) or CRaRb;

Ra and Rb are independently selected from H, alkyl, aralkyl, OR, NR'R" or Ra and Rb together optionally form a 3-7 membered cyclic ring which optionally contain a hetero atom selected from O, N or S;

Ra or Rb optionally form a cyclic ring with R3 or R4;

R1 and R2 are independently selected from H, alkyl, aryl, aralkyl, hydroxyalkyl, alkoxyalkyl, nitro, cyano, OR, NR'R" or R1 and R2 together optionally form a 3-7 membered cyclic ring which optionally contain a hetero atom selected from O or S;

R3 and R4 are independently selected from H, alkyl, aryl, aralkyl, hydroxyalkyl, alkoxyalkyl, COORa, C(O)R, C(O)NR'R" or R3 and R4 together optionally form a 3-7 membered cyclic ring which optionally contain a hetero atom selected from O, N or S;

R, R' and R" are selected from the group consisting of H, alkyl, aryl, aralkyl and acyl; and R5 is independently selected from the group consisting of H, alkyl, alkenyl, alkynyl, aryl, aralkyl, alkylsulfonyl, arylsulfonyl, hydroxyalkyl or alkoxyalkylacyl.

In another embodiment, the present invention relates to a simple and efficient process for preparation of novel tricyclic compounds of Formula I or its stereoisomers or esters or pharmaceutically acceptable salts thereof comprising the steps of:
a. degassing a mixture of compound (II) in toluene in a stream of argon and treating with Grubbs' I generation catalyst with stirring to obtain a mixture;
b. adding freshly distilled DMAD and DDQ to the mixture of step (a) followed by purification to obtain intermediate compound of Formula (III);
c. adding KOH to a solution of step (b) in EtOH-water mixture with stirring followed by heating the mixture with ethylene glycol and urea at a temperature in the range of 150-200° C. to afford compound of Formula I.

The general process is depicted in Scheme I:

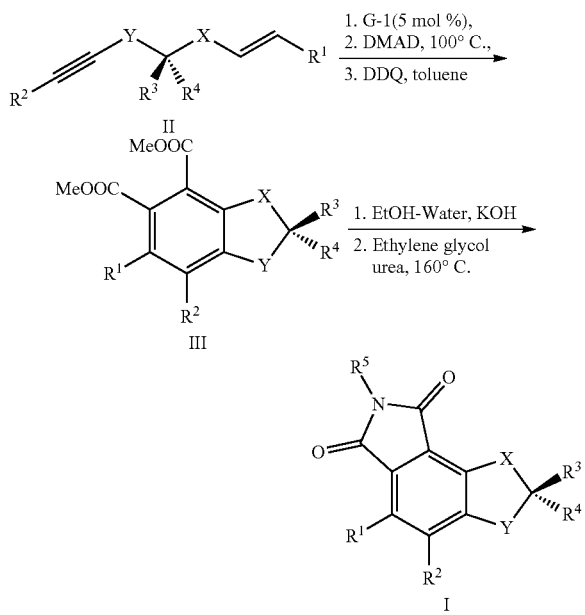

wherein
X and Y represent the group C(O) or CRaRb;
Ra and Rb are independently selected from H, alkyl, aralkyl, OR, NR'R" or Ra and Rb together optionally form a 3-7 membered cyclic ring which optionally contain a hetero atom selected from O, N or S;
Ra or Rb optionally form a cyclic ring with R3 or R4;
R1 and R2 are independently selected from H, alkyl, aryl, aralkyl, hydroxyalkyl, alkoxyalkyl, nitro, cyano, OR, NR'R" or R1 and R2 together optionally form a 3-7 membered cyclic ring which optionally contain a hetero atom selected from O or S;
R3 and R4 are independently selected from H, alkyl, aryl, aralkyl, hydroxyalkyl, alkoxyalkyl, COORa, C(O)R, C(O)NR'R" or R3 and R4 together optionally form a 3-7 membered cyclic ring which optionally contain a hetero atom selected from O, N or S;
R, R' and R" are selected from the group consisting of H, alkyl, aryl, aralkyl and acyl;
R5 is independently selected from the group consisting of H, alkyl, alkenyl, alkynyl, aryl, aralkyl, alkylsulfonyl, arylsulfonyl, hydroxyalkyl and alkoxyalkylacyl.

In another embodiment, the present invention relates to detailed process for preparation of various tricyclic compounds of formula I.

Accordingly, the present invention discloses a process for preparation of compound (7) and (8) in its racemate form, from compound of Formula (5) comprising;
a. degassing a mixture of compound (5) in toluene by passing stream of argon and treating with Grubbs' I generation catalyst with stirring at a temperature in the range of 30-60° C. to obtain a mixture;
b. adding freshly distilled DMAD and DDQ to mixture of step (a) to afford product (6);
c. adding KOH to a solution of compound (6) of step (b) in EtOH-water mixture with stirring to obtain crude 3-(benzyloxy)-5-(methoxycarbonyl)-2,2,6-trimethyl-2,3-dihydro-1H-indene-4-carboxylic acid;
d. taking crude product of step (c) in ethyleneglycol and adding urea with heating to afford pure 8-(benzyloxy)-4,7,7-trimethyl-7,8-dihydrocyclopenta[e]isoindole-1,3(2H,6H)-dione (7);
e. deprotection of benzyl group of compound (7) of step (d) with 10% Pd/C in ethanol to obtain racemate compound (8).

In an embodiment, the compound (5) is obtained from compound 2,2-dimethylpent-4-ynal (4), comprising the steps of;
a. adding 1-propenyl magnesium bromide to a mixture of 2,2-dimethylpent-4-ynal (4) in dry diethyl ether at 0° C. to obtain crude intermediate (E)-5,5-dimethyloct-2-en-7-yn-4-ol;
b. dissolving the crude intermediate of step (a) in THF followed by addition of metal hydride and benzyl bromide (BnBr) to obtain compound (5) as ~3:2 E, Z mixture.

The compound of formula (4) is prepared from the ester (1) by a process known in the art. The process for preparation of compounds (7) and (8) is depicted in Scheme 2 below:

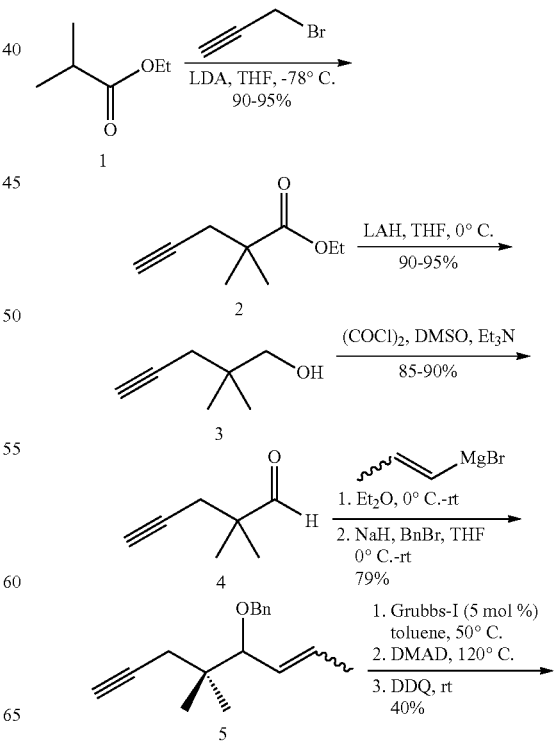

-continued

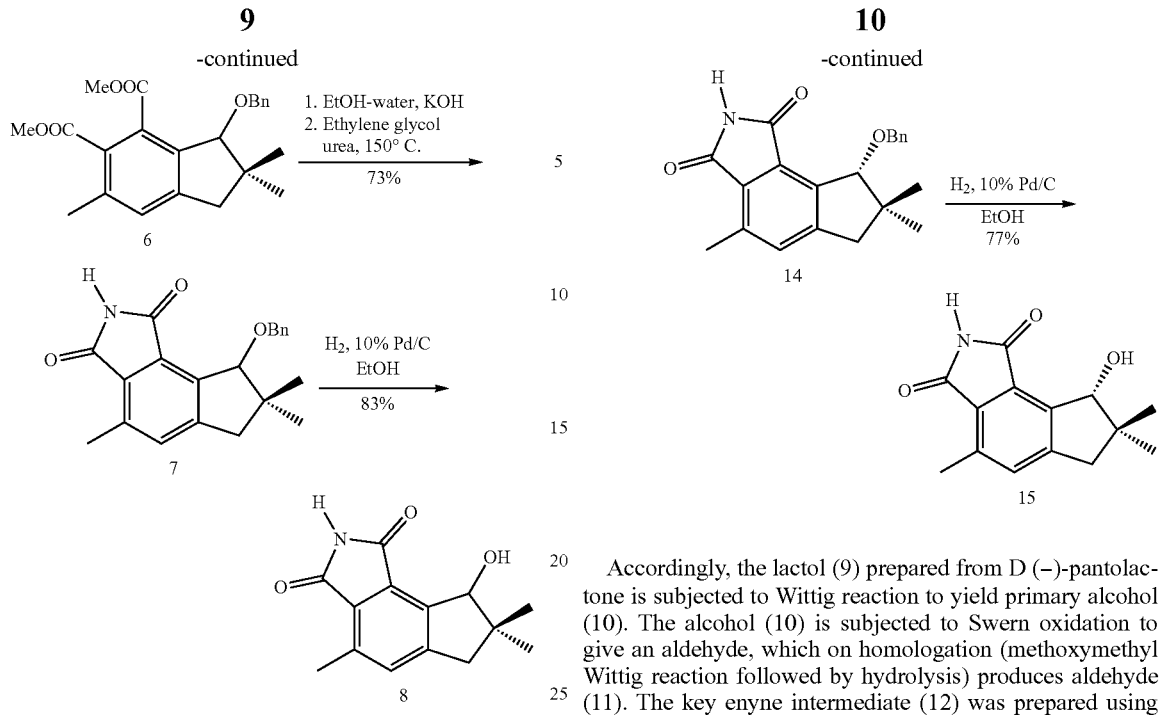

To ascertain the absolute configuration of the secondary alcohol in compound (8), the present invention discloses the preparation using D (−)—pantolactone as the starting material. The process is depicted in Scheme 3 below:

Scheme 3:

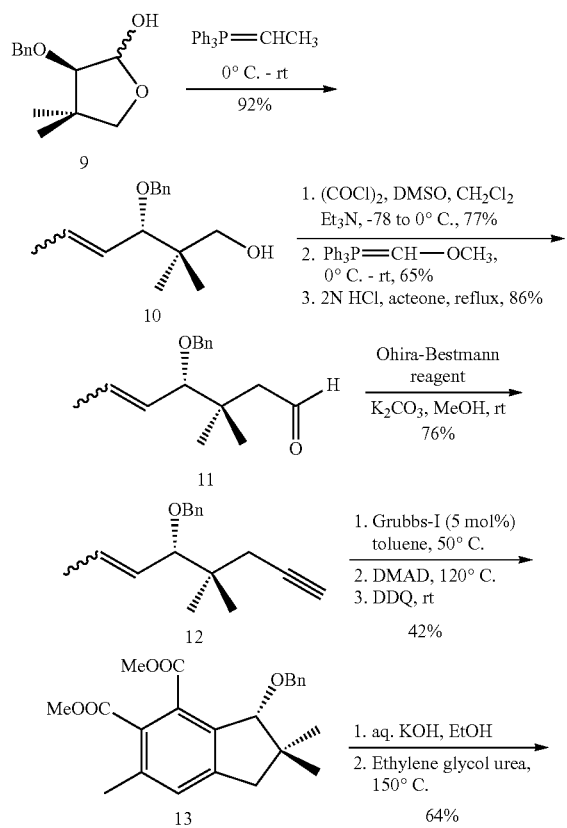

Accordingly, the lactol (9) prepared from D (−)-pantolactone is subjected to Wittig reaction to yield primary alcohol (10). The alcohol (10) is subjected to Swern oxidation to give an aldehyde, which on homologation (methoxymethyl Wittig reaction followed by hydrolysis) produces aldehyde (11). The key enyne intermediate (12) was prepared using the Ohira-Bestmann reagent in which the aldehyde arm of (11) was transformed to the corresponding alkyne. The compound (12) was transformed to the target compound by using the same protocol developed for the synthesis of the racemate (±)-8 through the intermediate (−)-13 and (+)-14 (Scheme 2). The optical rotation of the synthesized (−)-8 was found to be comparable but with the opposite sign. This confirms the absolute configuration of the secondary alcohol present in the product as 'S'.

In another embodiment, the present invention relates to preparation of compounds (18) and (19) from compound (16) as depicted in Scheme 4 below: The process step comprises;
a. adding maleimide to a solution of compound (16) in toluene and heating the mixture, concentrating under reduced pressure to obtain (17);
b. adding a solution of bromine in DCM to a solution of (17) in anhy. DCM, stirring at 0° C. to r.t and evaporating the solvent to obtain crude dibromo compound; dissolving the dibromo compound in acetonitrile followed by addition of DBU to afford compound (18);
c. adding K$_2$CO$_3$ and bromo ethanol to compound 18 in DMF and heating to obtain compound (19).

Scheme 4:

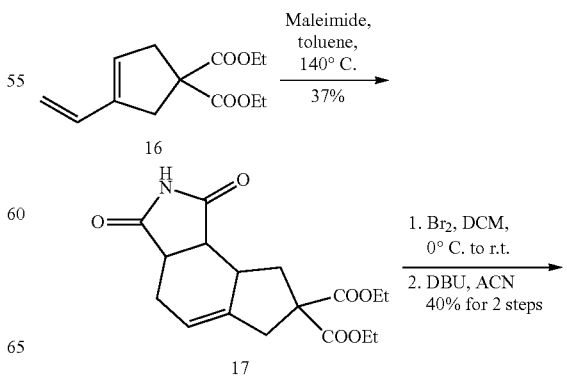

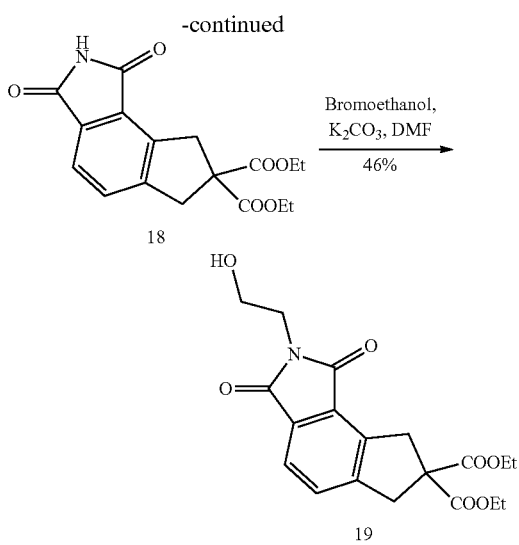

Accordingly, to a solution of compound (16) in toluene, was added maleimide and heated at 120° C. for 10 h. The reaction mixture was concentrated under reduced pressure to furnish (17). Further, solution of bromine in DCM was added to a solution of (17) in anhy. DCM and the mixture were stirred at room temperature (r.t). The solvent was evaporated to obtain crude dibromo compound. To the solution of dibromo compound in acetonitrile was added DBU at r.t to afford compound (18). To a solution of compound (18) in DMF, $K_2CO_3$ followed by bromo ethanol was added and heated at 50° C. to obtain compound (19).

In an embodiment, the compound (16) is obtained by a process disclosed in *Org. Lett., Vol.* 5, No. 19, 2003.

In yet another embodiment, the present invention relates to a process for preparation of compounds (22) and (23) and (24) from compound (20) as depicted in Scheme 5 below. The process step comprises:

a. adding maleimide to a solution of compound (20) in toluene and heating the mixture, concentrating under reduced pressure to obtain (21);

b. adding a solution of bromine in DCM to a solution of (21) in anhy. DCM, stirring at 0° C. to r.t and evaporating the solvent to obtain crude dibromo compound; dissolving the dibromo compound in acetonitrile followed by addition of DBU t to afford compound (22);

c. adding $K_2CO_3$ and bromo ethanol to one part of compound (22) in DMF and heating to obtain compound (23);

d. reacting the other part of compound (22) with metal hydride in THF followed by addition of 4-fluorobenzene sulfonyl chloride to obtain compound (24).

Scheme 5:

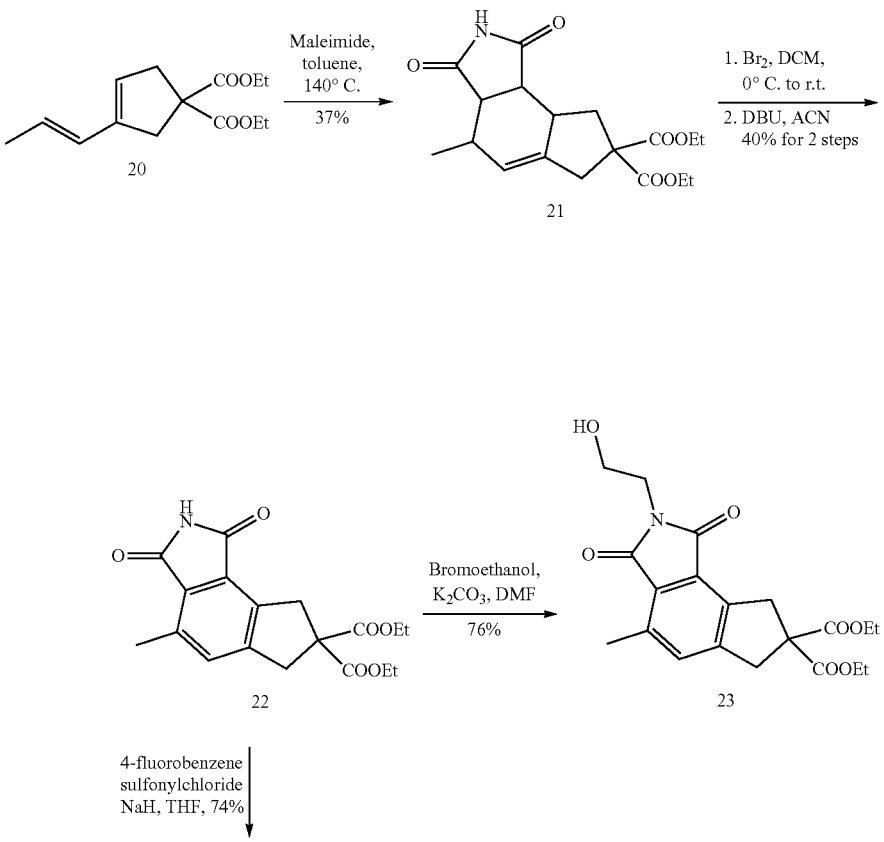

-continued

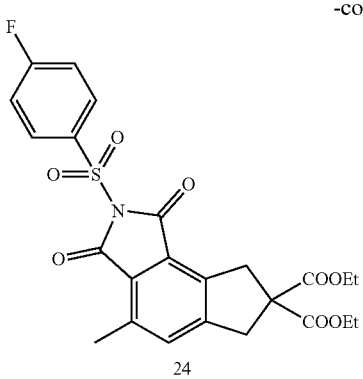

24

Accordingly, to a solution of compound (20) in toluene, was added maleimide and heated at 120° C. for 10 h. The reaction mixture was concentrated under reduced pressure to furnish (21). Further, solution of bromine in DCM was added to a solution of (21) in anhy. DCM and the mixture were stirred at room temperature (r.t). The solvent was evaporated to obtain crude dibromo compound. To the solution of dibromo compound in acetonitrile was added DBU at r.t to afford compound (22). To one part of solution of compound (22) in DMF, K₂CO₃ followed by bromo ethanol was added and heated at 50° C. to obtain compound (23). To the second part of solution of compound (22) was added sodium hydride in THF followed by addition of 4-fluorobenzene sulfonyl chloride to obtain compound (24).

In an embodiment, the process for preparation of compound (20) by a process (alkylations followed by enyne ring-closing metathesis reactions) disclosed in *Org. Lett., Vol. 5, No. 19, 2003*.

In yet another embodiment, the present invention relates to a process for preparation of compound (28) from compound (25) as depicted in Scheme 6 below. The process steps include;
  a. Adding to a stirred solution of diisopropyl amine in THF, n-BuLi at 0° C. stirring and further cooling to −78° C. followed by addition of compound (25) and acetic anhydride to afford compound (26);
  b. Adding DMAD, toluene to compound (26) taken in a sealed tube, heating, cooling followed by addition of DDQ to afford compound (27);
  c. Adding to the crude (27) in ethanol-water mixture ethylene glycol and urea and heating the mixture to afford compound (28).

Scheme 6:

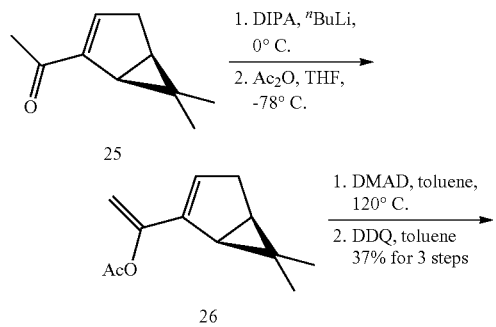

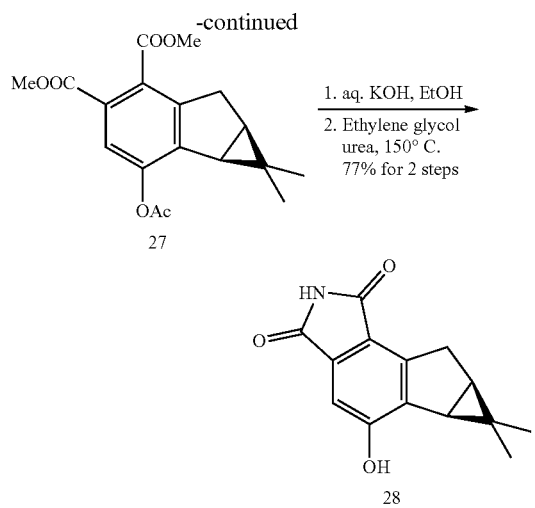

Accordingly, to a stirred solution of diisopropyl amine in THF was added n-BuLi at 0° C. and stirred for about 30 min and further cooled to −78° C. This was followed by addition of compound (25) and the mixture was stirred for another 25-40 min. Acetic anhydride was added and stirring was continued. Reaction mixture was quenched with saturated ammonium chloride, extracted in organic solvent, concentrated the organic layers to afford crude compound (26).

Above compound 26 was taken in a sealed tube and was added DMAD, toluene and heated at about 120° C. for about 12 hours. The reaction mixture was cooled, DDQ was added and stirring continued for another 12 hours at room temperature. Reaction mixture was filtered diluted, washed concentrated under reduced pressure to afford compound (27).

To the crude product 27 in ethanol-water mixture was added ethylene glycol and urea and the mixture was heated at about 150° C. to afford compound (28).

In an embodiment, the compound (25) is prepared by a process disclosed in *J. Org. Chem.* 2003, 68, 4727-4742.

In another embodiment, the present invention discloses the preparation compounds (30), (32) and (33) as depicted in Scheme 7 below. The process comprises;
  a. Adding portion wise compound (29) to a stirred, cold (10° C.) solution of fuming nitric acid and concentrated aqueous sulfuric acid by maintaining the temperature between 10 and 15° C.;

b. Stirring the mixture at same temperature and pouring the mixture onto ice, extracting, concentrating under reduced pressure to obtain (30) and (31) as yellow solid in 3:1 ratio;
c. Reacting the major compound (30) with stannous chloride in HCl to obtain amino compound (32);
d. Reacting compound (32) with XPHOS in presence of Pd$_2$(dba)$_3$, toluene and base to obtain compound (33).

Scheme7:

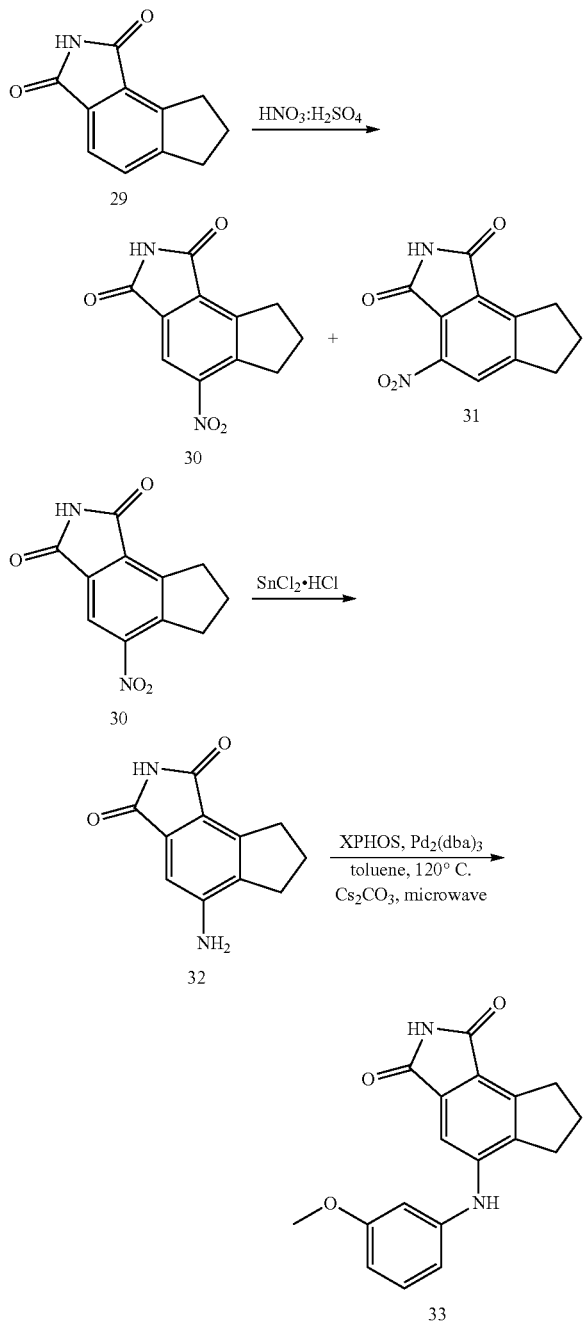

Accordingly, to a stirred, cold (10° C.) solution of fuming nitric acid and concentrated aqueous sulfuric acid was added, portionwise, compound (29) at a rate such that the temperature of the mixture was maintained between 10 and 15° C. The mixture was allowed to stir at same temperature for 3 hours. The yellow solution was slowly poured, with stirring, onto ice (5 gm) and stirred. The mixture was then extracted in a solvent, concentrated under reduced pressure and purified to obtain compounds (30) and (31) as yellow solids in 3:1 ratio. The major compound (30) was subjected to reduction in presence of SnCl$_2$/HCl to afford amine (32).

The compound (32) was reacted with XPHOS in presence of Pd$_2$(dba)$_3$, in toluene and a base and heated in microwave oven to afford compound (33).

The compound (29) is obtained by a process (Diels-Alder reaction between DMAD & vinylcyclopentene, aromatization and conversion of diesters to cyclic urea) disclosed in *Bioorganic & Medicinal Chemistry Letters* 16 (2006) 938-942.

In another embodiment, the present invention relates to a pharmaceutical composition comprising compound of formula (I), or a stereoisomer, or ester or pharmaceutically acceptable salt thereof, and a pharmaceutically acceptable carrier, diluent or excipient with anti-cancer, anti-bacterial, anti-viral, anti-fungal, central nervous system indications, cardio vascular system indications and suchlike.

The pharmaceutical compositions of the invention can be prepared by combining a compound of the invention with an appropriate pharmaceutically acceptable carrier, diluent or excipient, and may be formulated into preparations in solid, semi-solid, liquid forms, such as tablets, capsules, powders, granules, ointments, solutions, injections, gels and microspheres, In another embodiment, the present invention relates to a method for treating the subject suffering from cancer comprising administering 'an effective amount' of the pharmaceutical composition of compound of formula (I) its stereoisomer, or pharmaceutically acceptable salts thereof.

The present invention further relates to a method for treating the subject suffering from cancer or other disorders comprising administering therapeutic amount of the pharmaceutical composition of compound of formula I, its stereoisomer, or pharmaceutically acceptable salts thereof.

Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The pharmaceutical compositions of the invention may be administered to a subject or patient in need of the same, when indicated in conditions, diseases or disorders other than cancer selected from, but not limited to anti-bacterial, anti-viral, anti-fungal, central nervous system indications, cardio vascular system indications and suchlike.

In yet another embodiment, the present invention relates to the use of pharmaceutical composition of compound of formula I its stereoisomer, or pharmaceutically acceptable salts thereof for treatment of cancer or other disorders thereof.

The following examples, which include preferred embodiments, will serve to illustrate the practice of this invention, it being understood that the particulars shown are by way of examples and for purpose of illustrative discussion of preferred embodiments of the invention only and are not limiting the scope of the invention.

EXAMPLES

Example 1

Preparation of (((5,5-Dimethyloct-2-en-7-yn-4-yl) oxy)methyl)benzene (5)

To a solution of 2,2-dimethylpent-4-yn-1-al (4) (2.0 g, 18 mmol) in dry diethyl ether (50 mL) 1-propenyl magnesium bromide (0.5M in THF, 44 mL, 22 mmol) was added slowly at 0° C. and stirred for 1 h. The reaction mixture was quenched by addition of saturated aqueous ammonium chloride (30 mL), organic layer was separated and the aqueous layer was extracted with diethyl ether (50 mL×2). Combined organic layer was washed with brine solution (30 mL), dried over $Na_2SO_4$ and solvent was evaporated under reduced pressure to afford 2.2 g of crude 5,5-dimethyloct-2-en-7-yn-4-ol.

To a suspension of NaH (1.4 g, 36 mmol, 60% in mineral oil) in dry DMF (50 mL) was added above obtained alcohol in DMF (10 mL) at 0° C. After being stirred at 0° C. for 30 min, BnBr (2.2 mL, 18 mmol) and TBAI (670 mg, 1.8 mmol) was added at 0° C. and the mixture was stirred at r.t for 2 h. Water (30 mL) was added and extracted with diethyl ether (50 mL×3). The organic layer was washed with brine solution (20 mL), dried over $Na_2SO_4$, evaporated in vacuo. The residue was purified by column chromatography (2% ethyl acetate in hexanes) to afford (5)(3.5 g, 79%, pale yellow liquid) as ~3:2 E, Z mixture. IR$v_{max}$ (film): 3306, 2968, 2938, 2359,1506 cm-1; 1H NMR (400 MHz, CDCl3) (mixture of E, Z): δ 7.39-7.34 (m, 8H), 7.33-7.27 (m, 2H), 5.95-5.81 (m, 1H), 5.79-5.65 (m, 1H), 5.52-5.35 (m, 2H), 4.66-4.53 (m, 2H), 4.39-4.26 (m, 2H), 4.12-4.00 (m, 1H), 3.58 (d, J=8.7 Hz, 1H), 2.43-2.30 (m, 2H), 2.26-2.17 (m, 2H), 2.05-1.91 (m, 2H), 1.81 (td, J=6.8, 1.4 Hz, 3H), 1.71 (td, J=7.1, 1.3 Hz, 3H), 1.08-1.03 (m, 6H), 1.03-0.97 (m, 6H); 13C NMR (100 MHz, CDCl3): δ 139.2, 139.1, 130.7, 129.6, 128.1, 128.0, 127.6, 127.5, 127.2, 127.1, 85.7, 82.6, 78.5, 70.1, 70.0, 69.8, 69.7, 38.2, 37.6, 29.0, 28.9, 23.5, 23.1, 22.4, 22.1, 17.9, 13.7; MS: 265 (M+Na)+; HRMS calculated for $C_{17}H_{22}ONa$: 265.1563. found 265.1561.

Example 2

Preparation of dimethyl 3-(benzyloxy)-2,2,6-trimethyl-2,3-dihydro-1H-indene-4,5-dicarboxylate (6)

A solution of compound (5) (0.5 g, 2.0 mmol) in toluene (5 mL) was degassed for 10 min in a stream of argon and then treated with Grubbs' 1st generation catalyst (85 mg, 5 mol %) in one portion. After being stirred at 50° C. for 12 h, reaction mixture was cooled to room temperature and freshly distilled dimethyl acetylenedicarboxylate (DMAD) (0.5 mL, 4.1 mmol) was added and heated at 120° C. for 10 h. Cooled to room temperature, DDQ (562 mg, 2.5 mmol) was added and stirred for 8 h, reaction mixture was filtered through celite pad and washed with dichloromethane, filtrate was evaporated to dryness and the crude product was purified by column chromatography (5% ethyl acetate in hexanes) to furnish (6) (0.32 g, 40% for three steps); IR $v_{max}$(film): cm-1 2925, 1732, 1435, 1267; ¹H NMR (500 MHz, CDCl3): δ 7.37-7.29 (m, 5H), 7.19 (s, 1H), 4.86 (s, 1H), 4.70 (d, J=11.3 Hz, 1H), 4.58 (d, J=11.3 Hz, 1H), 3.90 (s, 3H), 3.73 (s, 3H), 2.95 (d, J=15.9 Hz, 1H), 2.60 (d, J=15.9 Hz, 1H), 2.40 (s, 3H), 1.28 (s, 3H), 1.17 (s, 3H); 13C NMR (125 MHz, CDCl3): δ 169.2, 168.0, 146.4, 140.6, 138.8, 136.9, 131.0, 129.9, 129.1, 128.3, 128.2, 127.4, 127.3, 89.1, 73.0, 52.3, 52.2, 45.5, 44.5, 28.0, 22.7, 20.0; MS: 405 (M+Na)+; HRMS calculated for $C_{23}H_{26}O_5Na$ 405.1672. found 405.1670.

Example 3

Preparation of 8-(Benzyloxy)-4,7,7-trimethyl-7,8-dihydrocyclopenta [e]isoindole-1,3(2H,6H)-dione (7)

To a solution of (6) (80 mg, 0.2 mmol) in EtOH (2 mL), KOH (35 mg, 0.62 mmol, in 0.5 mL water) was added and stirred for 3 h at room temperature. Solvent was removed under reduced pressure and the residue was acidified with 1N HCl (pH-3) and extracted with ethyl acetate (10 mL×2). The combined organics were dried over anhydrous $Na_2SO_4$, concentrated under reduced pressure to afford crude acid.

The above acid was further taken in ethylene glycol (0.5 mL), urea (12 mg, 0.2 mmol) was added and heated at 150° C. for 2 h. The reaction mixture was cooled to room temperature, quenched with water (5 mL) and extracted with ethyl acetate (10 mL×2). Combined organic layers were washed with brine solution (5 mL) and dried over $Na_2SO_4$. The crude material obtained after removal of solvent was purified by column chromatography (10% ethyl acetate in hexanes) to afford 8-(benzyloxy)-4,7,7-trimethyl-7,8-dihydrocyclopenta[e]iso-indole-1,3(2H,6H)-dione (7)(51 mg, 73%) as a colorless sticky liquid. IR vmax(film): cm-1 3647, 3445, 2923, 1635, 1731,1457; ¹H NMR (400 MHz, CDCl3): δ 8.01 (bs, 1H), 7.41-7.18 (m, 6H), 4.84-4.75 (m, 2H), 4.75-4.58 (m, 1H), 3.08 (d, J=16.3 Hz, 1H), 2.69 (s, 3H), 2.52 (d, J=16.3 Hz, 1H), 1.40 (s, 3H), 0.99 (s, 3H); 13C NMR (100 MHz, CDCl3): δ 169.1, 168.5, 153.2, 139.1, 138.9, 138.8, 133.2, 129.7, 128.1, 127.7, 127.5, 127.3, 86.0, 72.6, 44.9, 27.3, 22.4, 17.8; MS: 358 (M+Na)+; HRMS calculated for $C_{21}H_{21}O_3NNa$ 358.1414. found 358.1412.

Example 4

Preparation of 8-Hydroxy-4,7,7-trimethyl-7,8-dihydrocyclopenta[e]isoindole-1,3(2H,6H)-dione (8)

To a solution of (7)(40 mg, 0.1 mmol) in EtOH (2 ml), 10% Pd/C (10 mg) was added and stirred for 10 h under H2 atmosphere. The reaction mixture was filtered, concentrated under reduced pressure and purified by column chromatography (12% ethyl acetate in hexanes) to afford 8-hydroxy-4,7,7-trimethyl-7,8-dihydrocyclopenta[e]isoindole-1,3-(2H, 6H)-dione (8) (24 mg, 83%) as a white solid. mp 148-150° C.; IR $v_{max}$(film): cm-1 3733, 1716, 1738, 1652, 1456; 1H NMR (400 MHz, CDCl3): δ 7.86 (bs, 1H, NH proton), 7.25 (s, 1H), 5.08 (s, 1H), 4.52 (s, 1H, OH proton), 2.81-2.73 (m, 2H), 2.63 (s, 3H), 1.33 (s, 3H), 0.98 (s, 3H); 13C NMR (100 MHz, CDCl3): δ 170.1, 169.1, 149.4, 143.0, 138.3, 133.1, 128.8, 127.6, 81.0, 46.0, 45.8, 26.4, 21.4, 17.8. MS: 268 (M+Na)+; HRMS calculated for $C_{14}H_{15}O_3NNa$ 268.0944. found 268.0944.

Example 5

Preparation of (S)-3-(Benzyloxy)-2,2-dimethylhex-4-en-1-ol (10)

To a stirred solution of ethyl triphenylphosphonium iodide (31.0 g, 74.3 mmol) in dry THF (150 mL) was added n-BuLi (1.6 M in hexanes, 46.4 mL, 74.3 mmol) at 0° C. After stirring for 30 min, a solution of (3R)-3-(benzyloxy)-4,4-dimethyltetrahydrofuran-2-ol (9)(3.3 g, 14.8 mmol) in dry THF (30 mL) was added. After completion of addition, the reaction mixture was warmed to room temperature and stirred for overnight. The reaction mixture was cooled to 0° C., quenched by the addition of saturated ammonium chloride solution (30 mL) and extracted with ethyl acetate (50 mL×3). Combined organic layer was washed with water (20 mL), brine (20 mL) and dried over Na2SO4, concentrated under reduced pressure and purified by column chromatography (5% ethyl acetate in hexanes) to afford (S)-3-(benzyloxy)-2,2-dimethylhex-4-en-1-ol (10) (3.2 g, 92%) as a colorless oil. [□]D24+28.9 (c 2.2, CHCl3); IR vmax(film): cm-1 3446, 2961, 1668, 1496; $^1$H NMR (400 MHz, CDCl3): δ 7.38-7.28 (m, 5H), 5.75-5.61 (dq, J=15.2, 6.7 Hz, 1H), 5.54-5.37 (m, 1H), 4.60 (d, J=11.9 Hz, 1H), 4.28 (d, J=11.9 Hz, 1H), 3.58 (d, J=9.2 Hz, 1H), 3.54 (dd, J=10.8, 5.7 Hz, 1H), 3.37 (dd, J=11.0, 5.0 Hz, 1H), 2.97 (t, J=5.7 Hz, 1H), 1.80 (dd, J=6.4, 1.4 Hz, 3H), 0.89 (s, 6H); 13C NMR (100 MHz, CDCl3): δ 138.3, 131.4, 128.4, 127.8, 127.7, 127.6, 88.1, 71.6, 70.0, 38.7, 22.7, 19.9, 17.8; MS: 257 (M+Na)+; HRMS calculated for $C_{15}H_{22}O_2Na$ 257.1512. found 257.1508.

Example 6

Preparation of (S)-4-(Benzyloxy)-3,3-dimethylhept-5-enal (11)

To a cooled solution of oxalyl chloride (1.8 mL, 21.2 mmol) in DCM (30 mL) was added DMSO (3.0 mL, 42.7 mmol) at −78° C. After 20 min, a solution of (10) (2.5 g, 10.6 mmol) in DCM (12 mL) was added and stirred for 1 h. Triethylamine (8.9 mL, 64.1 mmol) was added and stirring was continued for 30 min. Reaction was quenched with water (30 mL) and extracted with DCM (50 mL×3). Combined organic layer was washed water (30 mL), brine (30 mL), dried over Na2SO4 and concentrated under reduced pressure to give (S)-3-(benzyloxy)-2,2-dimethylhex-4-enal (11)(1.90 g, 77%) as a colorless oil. [α]D24+26.8 (c 1.1, CHCl3); IR vmax(film): cm-1 2975, 1731, 1496, 1205; 1H NMR (200 MHz, CDCl3): δ 9.52 (s, 1H), 7.39-7.13 (m, 5H), 5.82-5.61 (m, 1H), 5.47-5.30 (m, 1H), 4.57 (d, J=12.1 Hz, 1H), 4.27 (d, J=12.1 Hz, 1H), 3.77 (d, J=8.7 Hz, 1H), 1.79 (dd, J=6.4, 1.5 Hz, 3H), 1.10 (s, 3H), 0.96 (s, 3H); 13C NMR (50 MHz, CDCl3): δ206.0, 138.4, 132.4, 128.3, 127.6, 127.5, 126.6, 83.8, 69.8, 49.9, 19.6, 17.9, 16.7. MS: 255 (M+Na)+; HRMS calculated for C15H20O2Na: 255.1356. found 255.1353.

To a stirred solution of (Methoxymethyl) triphenylphosphonium chloride (8.0 g, 23.2 mmol) in dry THF (120 mL) was added n-BuLi (1.6 M in hexanes, 14.5 mL, 23.2 mmol) at 0° C. After stirring for 30 min, a solution of (S)-3-(benzyloxy)-2, 2-dimethylhex-4-enal (1.8 g, 7.7 mmol) in dry THF (30 mL) was added. After completion of addition, reaction mixture was warmed to room temperature and stirred for overnight. The reaction mixture was cooled to 0° C., quenched by the addition of saturated ammonium chloride solution (25 mL) and extracted with ethyl acetate (50 mL×3). Combined organic layer was washed with water (20 mL), brine (20 mL), dried over $Na_2SO_4$, concentrated under reduced pressure and purified by column chromatography (5% ethyl acetate in hexanes) to give 1.3 g (65%) of ((S)-1-methoxy-3,3-dimethylhepta-1,5-dien-4-yl)oxy)methyl)benzene as a colorless oil.

To a solution of ((S)-1-methoxy-3,3-dimethylhepta-1,5-dien-4-yl)oxy)methyl)benzene (1.3 g, 5.0 mmol) in acetone (30 mL), 2N HCl (6.2 mL, 12.5 mmol) was added and then refluxed for 40 min. The reaction mixture was cooled to rt, water (20 mL) was added and extracted with ethyl acetate (50 mL×2). The combined organics were dried over Na2SO4, concentrated under reduced pressure and purified by column chromatography (5% ethyl acetate in hexanes) to afford 1.1 g (86%) of (S)-4-(benzyloxy)-3,3-dimethylhept-5-enal as a colourless oil. $[α]_D^{24}$+10.1 (c 0.7, CHCl3); IR $v_{max}$(film): cm-1 2965, 1705, 1496, 1268; $^1$H NMR (200 MHz, CDCl3): □9.79 (t, J=3.2 Hz, 1H), 7.44-7.19 (m, 5H), 5.75-5.55 (m, 1H), 5.49-5.26 (m, 1H), 4.54 (d, J=11.9 Hz, 1H), 4.23 (dd, J=11.8, 2.1 Hz, 1H), 3.41 (d, J=8.5 Hz, 1H), 2.49-2.14 (m, 2H), 1.77 (dd, J=6.3, 1.4 Hz, 3H), 1.14-0.96 (m, 6H); $^{13}$C NMR (100 MHz, CDCl3): δ 203.3, 138.7, 131.7, 128.3, 127.9, 127.8, 127.7, 127.4, 86.9, 70.0, 53.3, 38.4, 25.5, 23.5, 18.0; MS: 269 (M+Na)+; HRMS calculated for $C_{16}H_{22}O_2Na$ 269.1512. found 269.1508.

Example 7

Preparation of (S)-(((5,5-Dimethyloct-2-en-7-yn-4-yl)oxy)methyl)benzene (12)

A solution of (S)-4-(benzyloxy)-3,3-dimethylhept-5-enal (11) (4 g, 16.2 mmol) and dimethyl-1-diazo-2-oxopropylphosphonate (6.24 g, 32.4 mmol) in MeOH (40 mL) was treated with anhydrous K2CO3 (4.5 g, 32.4 mmol) at r.t and continued stirring for 16 h. The mixture was diluted with diethyl ether (100 mL) and washed successively with saturated NaHCO3 (20 mL), water (20 mL), brine (20 mL) and dried over Na2SO4. The solvent was removed in vacuo and the residue was purified on a column chromatography (2% ethyl acetate in hexanes) to furnish (S)-(((5,5-dimethyloct-2-en-7-yn-4-yl)oxy)methyl)benzene (12) (3.0 g, 76%) as a colorless oil. $[α]_D^{26}$+6.2 (c 1.0, CHCl3); IR $v_{max}$(film): cm-1 3307, 2961, 2359, 2130, 1590, 1473, 1065; 1H NMR (500 MHz, CDCl3): δ 7.34-7.28 (m, 4H), 7.26-7.24 (m, 1H), 5.72-5.60 (m, 1H), 5.44-5.33 (m, 1H), 4.56 (d, J=11.9 Hz, 1H), 4.32-4.25 (m, 1H), 3.53 (d, J=8.5 Hz, 1H), 2.34-2.24 (m, 1H), 2.21-2.11 (m, 1H), 1.97-1.89 (m, 1H), 1.76 (d, J=6.4 Hz, 3H), 1.01 (s, 3H), 0.97 (s, 3H); 13C NMR (125 MHz, CDCl3): δ139.2, 130.7, 128.1, 127.6, 127.5, 127.2, 127.1, 85.7, 82.7, 70.1, 69.8, 37.6, 29.0, 23.5, 22.4, 17.9; MS: 265 (M+Na)+; HRMS calculated for $C_{17}H_{22}ONa$ 265.1563. found 265.1561.

Example 8

Preparation of Dimethyl (R)-3-(benzyloxy)-2,2,6-trimethyl-2,3-dihydro-1H-indene-4,5-dicarboxylate (13)

The compound (13)(0.33 g, 42%) was synthesized from (12) by following the similar procedure mentioned for the synthesis of (6). The NMR data was found to be identical with compound (7); $[α]_D^{25}$-59.3 (c 1.7, CHCl$_3$).

Example 9

Preparation of (R)-8-(benzyloxy)-4, 7, 7-trimethyl-7,8-dihydrocyclopenta [e]isoindole-1,3(2H, 6H)-dione (14)

The compound (14) (56 mg, 64%) was prepared from (13) by following the similar procedure mentioned for the synthesis of (7). $[α]_D^{25}$+7.8 (c 0.2, CHCl3).

Example 10

Preparation of (R)-8-Hydroxy-4,7,7-trimethyl-7,8-dihydrocyclopenta[e]isoindole-1,3(2H, 6H)-dione (15)

The compound (15) (28 mg, 77%) was synthesized from (14) by following the similar procedure mentioned for the synthesis of compound (8). $[\alpha]_D^{26}$-21.4 (c 0.4, MeOH).

Example 11

Preparation of Diethyl 1,3-dioxo-2,3,3a,4,6,8,8a,8b-octahydrocyclopenta[e]isoindole-7,7(1H)-dicarboxylate (17)

To a solution of compound (16)(3.0 g, 12.6 mmol) in toluene (20 mL) maleimide (1.22 g, 12.6 mmol) was added and heated at 120° C. for 10 h. The reaction mixture was concentrated under reduced pressure and purified by column chromatography (20% ethylacetate in hexanes) to furnish (17)(1.5 g, 37% for two steps).
$^1$H NMR (200 MHz, CDCl$_3$): δ 8.34 (brs, 1H), 5.72 (dd, J=2.4, 4.7 Hz, 1H), 4.32-4.05 (m, 4H), 3.33-3.07 (m, 2H), 2.91 (brs, 2H), 2.79-2.63 (m, 3H), 1.31-1.17 (m, 6H).

Example 12

Preparation of Diethyl 1,3-dioxo-2,3,6,8-tetrahydrocyclopenta[e]isoindole-7,7(1H)-dicarboxylate (18)

A solution of Br$_2$ (0.12 ml, 2.42 mmol) in CH$_2$Cl$_2$(3 mL) was added to a solution of compound (17)(0.68 g, 2.02 mmol) in anhyd. CH2Cl2 (10 mL) at 0° C. The mixture was stirred for an additional 30 min at room temperature. Evaporated the solvent to give crude dibromo compound. A solution of DBU (0.65 mL, 5.05 mmol) was added to a solution of dibromide in acetonitrile (10 mL) at room temperature, and the mixture was stirred for 12 h at room temperature. H$_2$O (5 mL) was added and extracted with EtOAc (3×10 mL). The combined organic phase was washed with brine solution and dried (Na2SO4), and evaporated under reduced pressure to give compound (18) (270 mg, 40%) as off white solid. $^1$H NMR (400 MHz, CDCl$_3$): δ 8.08 (brs, 1H), 7.67 (d, J=7.6 Hz, 1H), 7.53 (d, J=7.6 Hz, 1H), 4.29-4.14 (m, 4H), 3.90 (s, 2H), 3.66 (s, 2H), 1.34-1.18 (m, 6H); $^{13}$C NMR (100 MHz, CDCl$_3$): δ170.9, 168.2, 149.1, 138.8, 131.8, 129.5, 127.9, 122.7, 62.1, 60.6, 40.2, 38.3, 14.0; MS: 332(M+H)+.

Example 13

Diethyl 2-(2-hydroxyethyl)-1,3-dioxo-2,3,6,8-tetrahydrocyclopenta[e]isoindole-7,7(1H)-dicarboxylate (19)

To a solution of compound (18) (86 mg, 0.25 mmol) in DMF (1.0 mL), K2CO3 (42 mg, 0.30 mmol) followed by bromoethanol (22 µL, 0.30 mmol) was added and heated at 50° C. for 2 h. Cooled the reaction mixture, water (1 mL) was added and extracted with ethyl acetate. Concentrated the organic fractions and purified by column chromatography (25% ethyl acetate in hexanes) to afford (45 mg, 46%) as a white solid.
1H NMR (400 MHz, CDCl3) δ=7.66 (d, J=7.6 Hz, 1H), 7.50 (d, J=7.6 Hz, 1H), 4.21 (q, J=7.1 Hz, 4H), 3.85 (s, 3H), 3.89 (s, 3H), 3.64 (s, 2H), 1.30-1.19 (m, 6H); $^{13}$C NMR (100 MHz, CDCl$_3$) δ=171.0, 169.0, 168.9, 149.0, 138.6, 131.2, 129.3, 127.3, 122.6, 62.2, 61.2, 60.7, 40.8, 40.3, 38.4, 14.1; MS: 376(M+H)+

Example 14

Preparation of Diethyl 4-methyl-1,3-dioxo-2,3,6,8-tetrahydrocyclopenta[e]isoindole-7,7(1H)-dicarboxylate (22)

The compound was synthesized from (20) by following the procedure for the synthesis of (17) and (18) in 40% yield. 1H NMR (400 MHz, CDCl3) δ=7.61 (brs., 1H), 7.31 (s, 1H), 4.23 (q, J=7.1 Hz, 4H), 3.87 (s, 2H), 3.61 (s, 2H), 2.64 (s, 3H), 1.34-1.23 (m, 6H); 13C NMR (100 MHz, CDCl3) δ =171.0, 168.8, 167.9, 148.8, 137.7, 136.4, 131.8, 62.1, 60.6, 40.1, 38.2, 17.6, 14.0; MS: 346(M+H)+

Example 15

Preparation of Diethyl 2-(2-hydroxyethyl)-4-methyl-1,3-dioxo-2,3,6,8-tetrahydrocyclopenta[e]isoindole-7,7(1H)-dicarboxylate (23)

The compound was synthesized from (22) obtained in example 14 by following the procedure for the synthesis of (19) in 76% yield. $^1$H NMR (400 MHz, CDCl$_3$) δ=7.34-7.22 (m, 1H), 4.20 (q, J=7.2 Hz, 4H), 3.84 (s, 6H), 3.58 (s, 2H), 2.62 (s, 3H), 1.31-1.20 (m, 6H); $^{13}$C NMR (100 MHz, CDCl$_3$) δ=171.1, 169.7, 168.9, 148.8, 137.5, 136.2, 131.7, 127.6, 127.3, 62.2, 61.4, 60.7, 40.7, 40.1, 38.2, 29.8, 17.8, 14.1; MS: 390(M+H)+.

Example 16

Preparation of Diethyl 2-((4-fluorophenyl)sulfonyl)-4-methyl-1,3-dioxo-2,3,6,8-tetrahydrocyclopenta[e]isoindole-7,7(1H)-dicarboxylate (24)

To a stirred solution of compound (22) obtained in example 14 (65 mg, 0.18 mmol) in dry THF (NaH, 60% in mineral oil, 9 mg, 0.20 mmol) followed by 4-fluorobenzene sulfonylchloride (40 mg, 0.20 mmol) was added at 0° C. and stirred for 2 hours. Ice cold water (2 mL) was added and extracted with ethyl acetate. Combined organic layers were washed with brine solution and dried (Na2SO4), concentrated and purified by column chromatography to afford compound (24) (70 mg, 74%) as a white solid. $^1$H NMR (400 MHz, CDCl3) δ 8.22-8.19 (m, 2H), 7.53 (s, 1H), 7.25-7.20 (m, 2H), 4.22-4.16 (m, 4H), 3.82 (s, 2H), 3.57 (s, 2H), 2.60 (S, 3H), 1.26-1.22 (m, 6H); $^{13}$C NMR (100 MHz, CDCl$_3$) δ=170.8, 163.5, 162.9, 150.4, 139.3, 137.9, 134.6, 134.6, 133.2, 131.5, 131.4, 126.5, 126.4, 116.9, 116.7, 62.3, 60.6, 40.2, 38.3, 18.1, 14.1; MS: 504(M+H)+.

Example 17

Preparation of Dimethyl (1aS,6aR)-2-acetoxy-1,1-dimethyl-1,1a,6,6a -tetrahydrocyclopropa[a]indene-4,5-dicarboxylate (27)

To a stirred solution of diisopropyl amine (0.93 mL, 6.66 mmol) in THF (5 mL) was added n-BuLi (1.6 M in hexanes, 2.1 mL, 6.66 mmol) at 0° C. and stirred for 30 min. Reaction mixture was cooled to −78° C. Compound (25) (500 mg, 3.33 mmol) was added and stirred for 30 min followed by addition of acetic anhydride (0.37 mL, 4.0 mmol) with continuous stirring for another 2 hours. Reaction mixture was quenched with saturated ammonium chloride (5 mL) and extracted with diethyl ether (3×10 mL). Concentrated the organic layers to afford crude compound (26).

Above compound (26) was taken in a sealed tube. DMAD (0.28 mL, 2.30 mmol), toluene (5 mL) were added and heated at 120° C. for 12 hours. Cooled the reaction mixture, DDQ (474 mg, 2.09 mmol) was added and stirring was continued for 12 hours at room temperature. The reaction mixture was filtered through Celite. Filtrate was diluted with EtOAc (20 mL) and washed with saturated sodium bicarbonate solution (10 mL) and brine (10 mL). organic layer was separated, concentrated under reduced pressure and purified by column chromatography to afford compound (27)(410 mg, 37% for 3 steps); $^1$H NMR (400 MHz, CDCl$_3$) δ 7.42 (s, 1H), 3.87 (s, 3H), 3.83 (s, 3H), 3.15 (dd, J=7.6, 18.1 Hz, 1H), 2.85 (d, J=17.9 Hz, 1H), 2.32 (s, 3H), 2.14 (dd, J=1.1, 6.6 Hz, 1H), 1.76-1.70 (m, 1H), 1.14 (s, 3H), 0.66 (s, 3H); $^{13}$C NMR (100 MHz, CDCl$_3$) δ=168.7, 168.6, 166.2, 148.0, 146.7, 141.9, 128.3, 127.7, 121.9, 52.6, 34.6, 31.5, 30.6, 26.7, 22.8, 20.9, 13.8.

Example 18

Preparation of (5bS,6aR)-5-hydroxy-6,6-dimethyl-5b,6,6a,7-tetrahydro-1H-cyclopropa[3,4]cyclopenta[1,2-e]isoindole-1,3(2H)-dione (28)

The compound was synthesized in 77% yield from (27) by following the procedure for synthesis of compound (7). $^1$H NMR (500 MHz, DMSO-d6) δ =10.83 (brs., 1H), 10.60 (brs., 1H), 6.95 (s, 1H), 3.18 (dd, J=7.3, 18.9 Hz, 1H), 2.93 (d, J=18.9 Hz, 1H), 2.33 (brs., 1H), 1.76 (t, J=6.6 Hz, 1H), 1.23-1.08 (m, 3H), 0.59 (s, 3H); $^{13}$C NMR (125 MHz, DMSO-d6) δ=169.9, 169.8, 159.4, 145.2, 136.9, 133.5, 118.9, 108.2, 34.0, 30.8, 30.2, 26.7, 22.2, 14.2; MS: 242 (M–H).

Example 19

Preparation of 5-nitro-7,8-dihydrocyclopenta[e]isoindole-1,3(2H,6H)-dione (30) and 4-nitro-7,8-dihydrocyclopenta[e]isoindole-1,3(2H,6H)-dione (31)

To a stirred, cold (0° C.) solution of fuming nitric acid in 2.0 mL of sulfuric acid 2.0 mL was added, portionwise, 175 mg (0.93 mmol) of phthalimide (29) maintaining the reaction temperature below 5° C. The mixture was allowed to stir at same temperature for 3 hours. The yellow solution was slowly poured, with stirring, onto ice (5 gm). Then extracted with ethylacetate, concentrated under reduced pressure and purified by column chromatography to obtain (30) and (31) as yellow solids in 3:1 ratio.

Compound 30: $^1$H NMR (400 MHz, CDCl$_3$) δ =8.45 (s, 1H), 8.16 (brs., 1H), 3.51 (t, J=7.6 Hz, 2H), 3.37 (t, J=7.7 Hz, 2H), 2.34 (quin, J=7.6 Hz, 2H). $^{13}$C NMR (125 MHz, CDCl$_3$) δ=166.6, 166.0, 149.7, 148.9, 147.7, 132.4, 130.8, 118.0, 34.2, 30.8, 25.3; MS: 231(M–H).

Example 20

Preparation of 5-amino-7,8-dihydrocyclopenta[e]isoindole-1,3(2H,6H)-dione (32)

To a stirred solution of SnCl$_2$(107 mg) in hydrochloric acid (2.0 mL) and H$_2$O (1.5 mL) was added compound (31) at 0° C. and stirred the reaction mixture for 2 hours. The solution was poured into 2N NaOH solution (5 mL). Then extracted with ethylacetate, concentrated under reduced pressure and purified by column chromatography to obtain (32) in 40% yield. $^1$H NMR (200 MHz, DMSO-d6) δ =10.54 (s, 1H), 6.74 (s, 1H), 6.11 (s, 2H), 2.99 (t, J=7.5 Hz, 2H), 2.64 (t, J=7.4 Hz, 2H), 2.14-1.98 (m, 3H); MS: 201 (M–H).

Example 21

5-(3-methoxyphenyl)amino)-7,8-dihydrocyclopenta[e]isoindole-1,3(2H,6H)-dione (33)

Compound (32) (22 mg, 0.11 mmol), XPHOS (0.05 eq.), Pd$_2$(dba)$_3$ (0.05 eq.), Cs$_2$CO$_3$ (0.15 mmol) and 3-bromoanisole (16 4, 0.13 mmol) were taken in toluene (2 mL) and heated at 120° C. under microwave for 35 min. Reaction mixture was extracted with ethylacetate (2×5 mL), washed with brine (4 mL) and purified by column chromatography to obtain compound (33) in 20% yield. $^1$H NMR (400 MHz, DMSO-d6) δ =10.79 (s, 1H), 8.20 (s, 1H), 7.28 (t, J=8.1 Hz, 1H), 7.17 (s, 1H), 6.81 (s, 1H), 6.75 (s, 1H), 6.66 (d, J=8.3 Hz, 1H), 3.75 (s, 3H), 3.14-3.01 (m, 2H), 2.84 (d, J=14.7 Hz, 2H), 2.14 (d, J=7.3 Hz, 2H); MS: 307 (M–H).

SRB Assay Protocol for Anticancer Activity:

Addition of cells: The human cancer cell lines Ovary (SK-OV-3), Lung (A549) and Breast (MCF-7) maintained in RPMI-1640 medium; Cervical (HeLa), Head & Neck (FaDu) and Colorectal adenocarcinoma (SW620) are maintained in DMEM medium. The enumerated cells are dispensed in a 96-well tissue culture plate. Each well receives 100 µl of the cell suspension containing 10,000-20,000 cells (depending upon the nature of cell line). The cells are then incubated at 37° C. in 5% CO$_2$ concentration for 24 h before addition of the test samples/standard drugs.

Addition of test samples: 100 µl of working solution of the test sample is added to the cell monolayer to give a final concentration 10 µM (pure compound) For each sample, duplicate wells are included.

Positive (Drug) and Negative (Vehicle) Controls: In every assay plate both positive and vehicle controls are included. In positive control well, adriamycin (Doxorubicin) is added at 10 µM concentration. In vehicle control wells, DMSO is added. In all assay wells the final concentration of DMSO is 0.1%. The plates are then incubated at 37° C. in 5% CO$_2$ concentration for 48 h.

Addition of SRB and Colorimetric reading: After 48 h incubation, cells attached to substratum of the plate are fixed by adding cold 50% trichloroacetic acid (TCA, 50 µl/well) on top of the medium and incubated at 4° C. for 1 h. After that the plate is gently washed 5 times with slow running tap water via plastic tubing to remove TCA, culture medium and dead cells. The water stream should not be injected very fast or directly on to the bottom of the wells as this can cause cell monolayer to detach. After washing, the plates are allowed to dry in air (plates can be stored for long periods at room temperature after fixing and drying step) To dry plates, 50 µl/well of SRB solution is added and left at room temperature for 30 min. At the end of the staining period, unbound SRB is removed by quickly rinsing plates 4-5 times with 1% (v/v) acetic acid. Plates are allowed to air-dry at room temperature (Stained and dried plates can be stored indefinitely at room temperature). 150 µl of 10 mM Tris base solution is added to each well and plate is shaken for 15 min on a gyratory shaker to solubilize the protein-bound dye. Alternatively, if a shaker is unavailable, SRB gets solubilized after 30 min in Tris base solution. Absorbance is measured at 510 nm in a microplate spectrophotometer.

Data Analysis

Percentage of cell growth inhibition in presence of the test sample is calculated as follows:

$$\% \text{ of cells killed} = 100 - \left[\frac{(\text{mean } OD_{test})}{(\text{mean } OD_{control})} \times 100\right]$$

TABLE 1

| | | Anti-cancer activity data: % Inhibition at 10 μM Solution in Cancer Cell Line | | | | | | | | | | | | |
|---|---|---|---|---|---|---|---|---|---|---|---|---|---|---|
| | | Breast | | Colon | | cervical | | Head & Neck | | Lung | | Ovary | | |
| S. No | Compound No | MCF-7 | MDA-MB-231 | DLD-1 | SW620 | COLO205 | HELA | C-33A | FADU | KB | NCI-A549 | NCI-H358 | H446 | SKOV3 | OVACR-3 | NIH:PA1 |
| 1 | 22 | 10.44 | 0.00 | 0.00 | 15.36 | 0.00 | 34.34 | 0.00 | 10.34 | 0.00 | 27.01 | 0.00 | 0.00 | −9.36 | 0.00 | 0.00 |
| 2 | 24 | 34.86 | 0.00 | 0.00 | 50.47 | 0.00 | 65.18 | 0.00 | 59.44 | 0.00 | 48.21 | 0.00 | 0.00 | 21.22 | 0.00 | 0.00 |
| 3. | 18 | 6.84 | 0.00 | 0.00 | 13.24 | 0.00 | 20.88 | 0.00 | −0.05 | 0.00 | 28.78 | 0.00 | 0.00 | −1.46 | 0.00 | 0.00 |
| 4. | 19 | 3.44 | 0.00 | 0.00 | 15.17 | 0.00 | 25.68 | 0.00 | 0.16 | 0.00 | 28.96 | 0.00 | 0.00 | −3.91 | 0.00 | 0.00 |
| 5 | 23 | 8.24 | 0.00 | 0.00 | 13.29 | 0.00 | 31.03 | 0.00 | 10.99 | 0.00 | 19.20 | 0.00 | 0.00 | −7.23 | 0.00 | 0.00 |
| 6 | 8 | 4.31 | 0.00 | 0.00 | −11.48 | 0.00 | 29.05 | 0.00 | 2.10 | 0.00 | 6.05 | 0.00 | 0.00 | 5.55 | 0.00 | 0.00 |
| | Doxorubicin (10 μM) Standard drug | 66.70 | 0.00 | 0.00 | 80.33 | 0.00 | 89.49 | 0.00 | 89.61 | 0.00 | 69.14 | 0.00 | 0.00 | 57.95 | 0.00 | 0.00 |

ADVANTAGES OF THE INVENTION

Novel compounds
Process provides a template that is more amenable to substitution
Synthetic process proposed for the first time
Anti-cancer agent

The invention claimed is:

1. A compound of Formula I or pharmaceutically acceptable salts or stereoisomer or ester thereof;

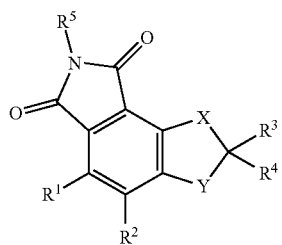

Formula I wherein,
X and Y represent the group C(O) or CRaRb;
Ra and Rb are independently selected from: H, alkyl, aralkyl, OR, NR'R" or Ra and Rb together optionally form a 3-7 membered cyclic ring which optionally contain a hetero atom selected from O, N, S, or, when a three membered cyclic ring is present, Ra or Rb form a substituted or unsubstituted cyclic ring with $R^3$ or $R^4$;
$R^1$ and $R^2$ are independently selected from H, alkyl, aryl, aralkyl, hydroxyalkyl, alkoxyalkyl, nitro, OR, NR'R" or, when a three membered cyclic ring is present between Y and $R^3$ or $R^4$, $R^2$ may also be a hydroxyl;

$R^3$ and $R^4$ are independently selected from H, alkyl, aryl, aralkyl, hydroxyalkyl, alkoxyalkyl, COOR, C(O)R, C(O)NR'R";
R is selected from the group consisting of alkyl, substituted or unsubstituted aryl, and aralkyl;
R' and R" are selected from the group consisting of H, alkyl, substituted or unsubstituted aryl, and aralkyl; and
$R^5$ is independently selected from the group consisting of H, alkyl, alkenyl, alkynyl, alkylsulfonyl, arylsulfonyl, hydroxyalkyl and alkoxyalkylacyl.

2. The compounds according to claim 1, selected from the group consisting of;
 i) 8-(Benzyloxy)-4,7,7-trimethyl-7,8-dihydrocyclopenta[e]isoindole-1,3(2H,6H)-dione (compound 7);
 ii) Diethyl 1,3-dioxo-2,3,6,8-tetrahydrocyclopenta[e]isoindole-7,7(1H)-dicarboxylate (compound 18);
 iii) Diethyl 2-(2-hydroxyethyl)-1,3-dioxo-2,3,6,8-tetrahydrocyclopenta[e]isoindole-7,7(1H)-dicarboxylate (compound 19);
 iv) Diethyl 4-methyl-1,3-dioxo-2,3,6,8-tetrahydrocyclopenta[e]isoindole-7,7(1H)-dicarboxylate (compound 22);
 v) Diethyl 2-(2-hydroxyethyl)-4-methyl-1,3-dioxo-2,3,6,8-tetra hydro cyclopenta[e]isoindole-7,7(1H)-dicarboxylate (compound 23);
 vi) Diethyl 2-((4-fluorophenyl)sulfonyl)-4-methyl-1,3-dioxo-2,3,6,8-tetra hydro cyclopenta[e]isoindole-7,7(1H)-dicarboxylate (compound 24);
 vii) (5bS,6aR)-5-hydroxy-6,6-dimethyl-5b,6,6a,7-tetrahydro-1H-cyclopropa[3,4]cyclopenta[1,2-e]isoindole-1,3(2H)-dione (compound 28);
 vii) 5-nitro-7,8-dihydrocyclopenta[e]isoindole-1,3(2H,6H)-dione (compound 30);
 ix) 4-nitro-7,8-dihydrocyclopenta[e]isoindole-1,3(2H,6H)-dione (compound 31);
 x) 5-amino-7,8-dihydrocyclopenta[e]isoindole-1,3(2H,6H)-dione (compound 32); and
 xi) 5-((3-methoxyphenyl)amino)-7,8-dihydrocyclopenta[e]isoindole-1,3(2H,6H)-dione (compound 33).

3. A process for the preparation of the compound of formula I or pharmaceutically acceptable salts or stereoisomer or ester according to claim 1, said process comprising:

a) degassing a mixture of compound II

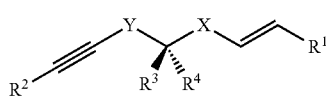
II in toluene in a stream of argon and treating with Grubbs' I generation catalyst with stirring to obtain a mixture;
b) adding freshly distilled DMAD and DDQ to the mixture of step (a) followed by purification to obtain intermediate compound of Formula III; and

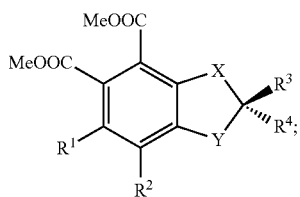
III c) adding KOH to a solution of intermediate compound of Formula III in an EtOH-water mixture with stirring followed by heating the mixture with ethylene glycol and urea at a temperature in the range of 150-200° C. to afford compound of Formula I.

4. The process for preparation of compound (7) according to claim 2, the process comprising the steps of;
a) degassing a mixture of (compound 5)

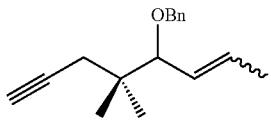

in toluene by passing stream of argon and treating with Grubbs' I generation catalyst with stirring at a temperature in the range of 30-60° C. to obtain a mixture;
b) adding freshly distilled DMAD and DDQ to the mixture of step (a) to afford compound (6)

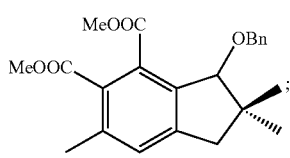

c) adding KOH to a solution of compound (6) of step (b) in an EtOH-water mixture with stirring to obtain crude 3-(benzyloxy)-5-(methoxycarbonyl)-2,2,6-trimethyl-2,3-dihydro-1H-indene-4-carboxylic acid; and
d) taking crude product of step (c) in ethylene glycol and adding urea with heating to afford.

(compound 7)

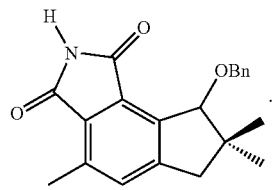

5. The process according to claim 4, wherein compound (5) is prepared by a process comprising the steps of;
a) adding 1-propenyl magnesium bromide to a mixture of 2,2-dimethylpent-4-ynal (4) in dry diethyl ether at 0° C. to obtain crude intermediate (E)-5,5-dimethyloct-2-en-7-yn-4-ol; and
b) dissolving the crude intermediate of step (a) in THF followed by addition of metal hydride and benzyl bromide (BnBr) to obtain compound (5) as ~3:2 E, Z mixture.

6. The process for preparation of compounds (18) and (19) as defined in claim 2, comprising the steps of;
a) adding maleimide to a solution of compound (16):

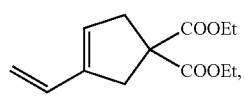
16 in toluene and heating the mixture, concentrating under reduced pressure to obtain compound (17):

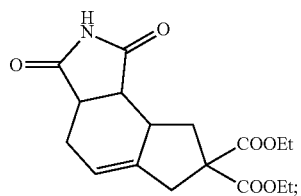
17 b) adding a solution of bromine in DCM to a solution of (17) in DCM, stirring at 0° C. to room temperature and evaporating the solvent to obtain a crude dibromo compound, dissolving the dibromo compound in acetonitrile followed by addition of DBU to afford compound (18); and
c) adding K₂CO₃ and bromo ethanol to compound (18) in DMF and heating to obtain compound 19.

7. A process for preparation of compounds (22), (23) and (24) as defined in claim 2, comprising the steps of;
a) adding maleimide to a solution of compound (20):

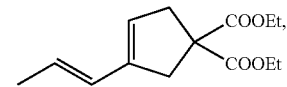
20 in toluene and heating the mixture, concentrating under reduced pressure to obtain compound (21):

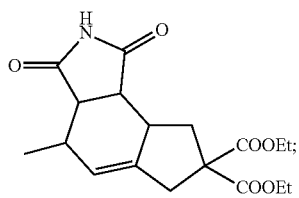

b) adding a solution of bromine in DCM to a solution of (21) in DCM, stirring at 0° C. to room temperature and evaporating the solvent to obtain a crude dibromo compound, dissolving the dibromo compound in acetonitrile followed by addition of DBU to afford compound (22);

c) adding K$_2$CO$_3$ and bromo ethanol to a portion of compound (22) obtained in step (b) in DMF and heating to obtain compound (23); and d) reacting a second portion of compound (22) obtained in step (b) with metal hydride in THF followed by addition of 4-fluorobenzene sulfonyl chloride to obtain compound (24).

8. The process for preparation of compound (28) as defined in claim 2, comprising the steps of;

a) adding to a stirred solution of diisopropyl amine in THF, n-BuLi at 0° C. stirring and further cooling to −78° C. followed by addition of compound (25):

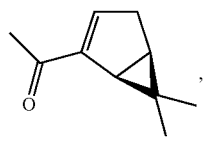

and acetic anhydride to afford compound (26):

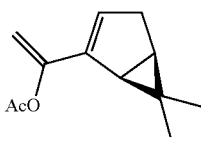

b) adding DMAD, toluene to compound (26) heating in a sealed tube and cooling followed by addition of DDQ to afford compound (27):

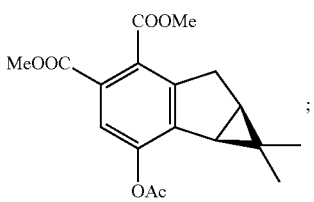

and c) adding to the crude (27) in ethanol-water mixture ethylene glycol and urea and heating the mixture to afford compound (28).

9. The process for preparation of compounds (30), (32) and (33) as defined in claim 2, comprising the steps of;

a) adding compound (29):

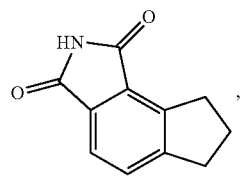

to a stirred, cold (10° C.) solution of fuming nitric acid and concentrated aqueous sulfuric acid by maintaining the temperature between 10 and 15° C.;

b) stirring the mixture at the same temperature and pouring the mixture onto ice, extracting, concentrating under reduced pressure to obtain compounds (30) and (31):

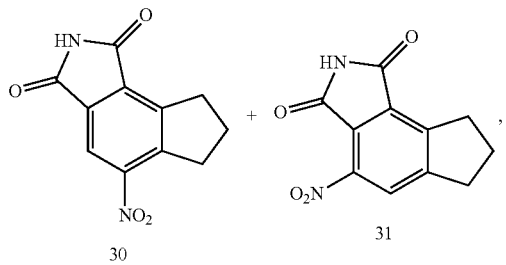

as yellow solid in 3:1 ratio;

c) reacting the major compound 30 with stannous chloride in HCl to obtain amino compound (32); and d) reacting compound (32) with XPHOS in presence of Pd$_2$(dba)$_3$, toluene and base to obtain compound (33).

10. A pharmaceutical composition comprising the compound of claim 1, optionally along with a pharmaceutically acceptable carrier.

11. A method for treating a subject suffering from cancer comprising administering to a subject in need thereof a therapeutic amount of the compound of claim 1.

* * * * *